United States Patent
Mackewitz

(10) Patent No.: US 6,559,344 B2
(45) Date of Patent: May 6, 2003

(54) HYDROFORMYLATION

(75) Inventor: Thomas Mackewitz, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/076,429

(22) Filed: Feb. 19, 2002

(65) Prior Publication Data
US 2002/0115892 A1 Aug. 22, 2002

(30) Foreign Application Priority Data

Feb. 19, 2001 (DE) ......................... 101 07 684

(51) Int. Cl.$^7$ .................... C07C 45/49; C07C 45/50
(52) U.S. Cl. .................. 568/429; 568/444; 568/451; 568/454; 568/489
(58) Field of Search ................ 568/429, 444, 568/451, 454, 489

(56) References Cited

U.S. PATENT DOCUMENTS

| | | | | |
|---|---|---|---|---|
| 4,169,861 A | 10/1979 | Hughes | ........ | 260/604 |
| 4,201,714 A | 5/1980 | Hughes | ........ | 260/340 |
| 4,201,728 A | 5/1980 | Hughes | ........ | 260/429 |
| 5,364,950 A | * 11/1994 | Babin et al. | | |

FOREIGN PATENT DOCUMENTS

WO      WO 95/30680      11/1995

OTHER PUBLICATIONS

Kranenburg et al. "New Diphosphine Ligands Based on Heterocyclic Aromatics Inducing Very High Regioselectivity in Rhodium–Catalyzed Hydroformylation: Effect of the Bite Angle" Organometallics vol. 14 pp. 3081–3089 (1995).

van der Veen et al. "New Phosphacyclic Diphosphines for Rhodium–Catalyzed Hydroformylation" Organometallics vol. 18 (1999) pp. 4765–4777.

Goertz et al. "Electronic Effects in the Nickel–Catalyzed Hydrocyanation of Styrene Applying Chelating Phosphorus Ligands with Large Bite Angels" J. Chem. Soc., Dalton Trans. (1998) pp. 2981–2988.

Haenel et al. Bidentate Phosphines of Heteroarenes: 4,6–Bis(diphenylphosphino)dibenzofuran and 4,6–(diphenylphosphino) dibenzothiophene[1,2]) Chem. Ber. Vol. 124(1991) pp. 1705–1710.

Hillebrand et al. Bidentate Phosphines of Heteroarenes: 9,9–Dimethyl–4,5–bis(diphenylphosphino)xanthene[1]) Tetrahedron Letters vol. 36 No. 1 (1995) pp. 75–78.

Haenel et al. Bidentate Phosphines of Heteroarenes: 1,9–Bis(diphenylphosphino)–dibenzothiophene and 4,6–Bis(diphenylphosphino)dibenzothiophene[1]) Tetrahedron Letters vol. 34 No. 1 (1993) pp. 2107–2110.

* cited by examiner

Primary Examiner—Johann Richter
Assistant Examiner—Sikarl A. Witherspoon
(74) Attorney, Agent, or Firm—Keil & Weinkauf

(57) ABSTRACT

In a process for the hydroformylation of ethylenically unsaturated compounds, at least one complex or compound of a metal of transition group VIII with at least one bidentate phosphine ligand is used as hydroformylation catalyst and at least one of the reaction steps following the hydroformylation reaction is carried out essentially in the absence of carbon monoxide and hydrogen and in the presence of at least one monodentate phosphine ligand.

8 Claims, No Drawings

HYDROFORMYLATION

The present invention relates to a process for the hydroformylation of ethylenically unsaturated compounds, in which at least one complex or compound of a metal of transition group VIII with at least one bidentate phosphine ligand is used as hydroformylation catalyst and at least one of the reaction steps following the hydroformylation reaction is carried out essentially in the absence of carbon monoxide and hydrogen and in the presence of at least one monodentate phosphine ligand.

Hydroformylation or the oxo process is an important industrial process and is employed for preparing aldehydes from olefins, carbon monoxide and hydrogen. These aldehydes can, if desired, be hydrogenated by means of hydrogen to form the corresponding oxo alcohols in the same process. The reaction itself is exothermic and generally proceeds under superatmospheric pressure and at elevated temperatures in the presence of catalysts. Catalysts used are Co, Rh, Ir, Ru, Pd or Pt compounds or complexes which may be modified with N- or P-containing ligands to influence the activity and/or selectivity. The hydroformylation reaction results in formation of mixtures of isomeric aldehydes because of the possible addition of CO onto each of the two carbon atoms of a double bond. In addition, double bond isomerization, i.e. a shift of an internal double bond to a terminal position or vice versa, can occur.

Owing to the substantially greater industrial importance of the α-aldehydes, optimization of the hydroformylation catalysts to achieve a very high hydroformylation activity combined with a very low tendency to form double bonds which are not in the α position is desired. In addition, there is a need for hydroformylation catalysts which lead to good yields of not only α-aldehydes but in particular n-aldehydes. For this purpose, the catalyst has to catalyze the hydroformylation of terminal olefins as selectively as possible.

The use of phosphorus-containing ligands for stabilizing and/or activating the catalyst metal in rhodium-catalyzed low-pressure hydroformylation is known. Suitable phosphorus-containing ligands are, for example, phosphines, phosphinites, phosphonites, phosphites, phosphoramidites, phospholes and phosphabenzenes. The most widely used ligands at present are triarylphosphines such as triphenylphosphine and sulfonated triphenylphosphine since these are sufficiently stable under the reaction conditions. However, these ligands have the disadvantage that, in general, only very high excesses of ligand give satisfactory yields, in particular of linear aldehydes. However, this generally reduces the activity.

In Tetrahedron Letters, volume 34, No. 13, page 2107 ff. (1993), in Tetrahedron Letters, volume 36, No. 1, page 75 ff. (1995) and in Chem. Ber. 124, page 1705 ff. (1991), Haenel et al. describe the synthesis of bis(diphenylphosphino) chelates having anthracene, dibenzofuran, dibenzothiophene and xanthene skeletons. Use of these compounds as catalysts is not described.

In J. Chem. Soc., Dalton Trans., 1998, pp. 2981–2988, W. Goertz et al. describe the use of chelating phosphines and phosphonites having a thioxanthene skeleton for the nickel-catalyzed hydrocyanation of styrene. Use in hydroformylation is not described.

In Organometallics 1999, 18, pages 4765 to 4777, van der Veen et al. describe the use of phosphacyclic diphosphines having a xanthene skeleton as ligands for rhodium-catalyzed hydroformylation. A disadvantage of these catalysts is their very low activity which makes use in industrial processes uneconomical.

WO 95/30680 describes bidentate phosphine ligands in which the phosphorus atoms can be bound to a xanthene skeleton and also describes the use of these ligands in catalysts for hydroformylation. A disadvantage of these catalysts is that they are not suitable for the isomerizing hydroformylation of internal olefins with good α- or n-selectivity.

In Organometallics 1995, 14, p. 3081–3089, M. Kranenburg et al. describe the influence of the angle of bite of bidentate phosphine ligands on the regioselectivity of rhodium-catalyzed hydroformylation. Mixed complexes of monodentate and bidentate phosphine ligands were also prepared.

A disadvantage of bidentate phosphine ligands in general and bidentate phosphines having a xanthene skeleton in particular is that the catalytically active species formed from them under the conditions of the hydroformylation reaction are generally not stable in the absence of synthesis gas ($CO/H_2$). It is generally not possible to convert catalyst species which have been deactivated in the absence of $CO/H_2$ back into an active hydroformylation catalyst. For this reason, continuous industrial hydroformylation processes which use catalysts based on bidentate phosphine ligands and encompass isolation of the hydroformylation products and recirculation of the catalyst can be implemented only with great technical difficulty, if at all. In any case, hydroformylation processes using such catalysts suffer from an economic disadvantage.

U.S. Pat. No. 4,169,861 describes a hydroformylation process for preparing 1-alkanals by hydroformylation of α-olefins using a rhodium complex based on a monodentate ligand and a bidentate ligand as catalyst. trans-1,2-Bis(diphenylphosphinomethyl)cycloalkanes and 1,1'-bis(diphenylphosphino)ferrocenes are described as suitable bidentate ligands. U.S. Pat. No. 4,201,728 makes disclosures similar to those of U.S. Pat. No. 4,169,861. U.S. Pat. No. 4,201,714 relates to a rhodium catalyst as used for hydroformylation according to U.S. Pat. No. 4,201,728. According to the three last-named documents, the use of a catalyst based on a monodentate ligand and a bidentate ligand leads to an improvement in the n/iso product selectivity in the hydroformylation of α-olefins. The use of monodentate phosphine ligands in highly selective hydroformylation catalysts based on bidentate phosphine ligands with the aim of stabilizing these catalysts even in the absence of synthesis gas is not described.

It is an object of the present invention to provide an improved process for the hydroformylation of compounds containing at least one ethylenically unsaturated double bond. The process should make it possible to separate off the desired products and recirculate the catalyst with very little drop in the activity of the catalyst used. The use of complicated measures for stabilizing the hydroformylation catalyst used when the desired products are separated off, possibly work-up of the catalyst before it is returned to the reaction, should preferably be able to be omitted. In particular, it should be possible to do without a synthesis gas atmosphere outside the reaction zone used for the hydroformylation. The hydroformylation of α-olefins should preferably result in a very high proportion of α-aldehydes or α-alcohols. In particular, the process should also have a high selectivity to n-products.

We have found that this object is achieved by a hydroformylation process in which the hydroformylation catalyst used comprises at least one complex or compound of a metal of transition group VIII with at least one bidentate phosphine ligand and at least one of the reaction steps following the hydroformylation reaction is carried out essentially in the absence of carbon monoxide and hydrogen and in the presence of at least one monodentate phosphine ligand. The bidentate phosphine ligand used is preferably a compound in which the two phosphine groups are each bound to a different phenyl ring of a xanthene skeleton.

The present invention accordingly provides a process for the hydroformylation of compounds containing at least one ethylenically unsaturated double bond by reaction with carbon monoxide and hydrogen in the presence of a catalyst system comprising at least one metal of transition group VIII and at least one bidentate phosphine ligand, which comprises (i) reacting the compound(s) containing at least one ethylenically unsaturated double bond in a reaction zone in the presence of carbon monoxide, hydrogen and the catalyst system, (ii) taking an output from the reaction zone and separating it into a fraction enriched in product and a fraction enriched in catalyst system, (iii) if desired, subjecting the fraction enriched in catalyst system obtained in step (ii) to work-up and (iv) returning at least part of the fraction enriched in catalyst system, if desired after work-up, to the reaction zone, where at least one of these steps (ii) to (iv) is carried out essentially in the absence of carbon monoxide and hydrogen and in the presence of at least one monodentate phosphine ligand.

The bidentate phosphine ligand is preferably selected from among compounds of the formula I

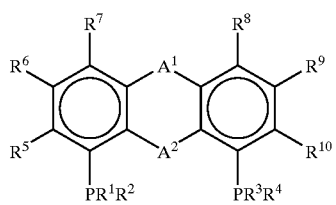

(I)

where $A^1$ and $A^2$ are each, independently of one another a single bond, O, S, $SiR^aR^b$, $NR^c$ or $CR^{11}R^{12}$, where $R^a$, $R^b$, $R^c$, $R^{11}$ and $R^{12}$ are each, independently of one another, hydrogen, alkyl, cycloalkyl, heterocycloalkyl, aryl or hetaryl, $R^1$, $R^2$, $R^3$ and $R^4$ are each, independently of one another, alkyl, cycloalkyl, heterocycloalkyl, aryl or hetaryl, which may each bear one, two or three substituents selected from among alkyl, cycloalkyl, heterocycloalkyl, aryl, hetaryl, $COOR^d$, $COO^-M^+$, $SO_3R^d$, $SO^-_3M^+$, $NE^1E^2$, alkylene-$NE^1E^2$, $NE^1E^2E^{3+}$ $X^-$, alkylene-$NE^1E^2E^{3+}X^-$, $OR^d$, $SR^d$, $(CHR^eCH_2O)_yR^d$, $(CH_2N(E^1))_yR^d$, $(CH_2CH_2N(E^1))_yR^d$, halogen, trifluoromethyl, nitro, acyl and cyano where $R^d$, $E^1$, $E^2$ and $E^3$ are identical or different radicals selected from among hydrogen, alkyl, cycloalkyl and aryl, $R^e$ is hydrogen, methyl or ethyl, $M^+$ is a cation, $X^-$ is an anion and y is an integer from 1 to 120, or $R^1$ and $R^2$ and/or $R^3$ and $R^4$ together with the phosphorus atom to which they are bound form a 5- to 8-membered heterocycle which may additionally be fused with one, two or three cycloalkyl, heterocycloalkyl, aryl or hetaryl groups, where the heterocycle and, if present, the fused-on groups may each bear, independently of one another, one, two, three or four substituents selected from among alkyl, cycloalkyl, heterocycloalkyl, aryl, hetaryl, $COOR^d$, $COO^-M^+$, $SO_3R^d$, $SO^-_3M^+$, $NE^1E^2$, alkylene-$NE^1E^2$, $NE^1E^2E^{3+}X^-$, alkylene-$NE^1E^2E^{3+}X^-$, $OR^d$, $SR^d$, $(CHR^eCH_2O)_yR^d$, $(CH_2N(E^1))_yR^d$, $(CH_2CH_2N(E^1))_yR^d$, halogen, trifluoromethyl, nitro, acyl and cyano, where $R^d$, $R^e$, $E^1$, $E^2$, $E^3$, $M^+$, $X^-$ und y are as defined above, $R^5$, $R^6$, $R^7$, $R^8$, $R^9$ and $R^{10}$ are each, independently of one another, hydrogen, alkyl, cycloalkyl, heterocycloalkyl, aryl, hetaryl, $COOR^f$, $COO^-M^+$, $SO_3R^f$, $SO^-_3M^+$, $NE^4E^5$, $NE^4E^5E^{6+}X^-$, alkylene-$NE^4E^5E^{6+}X^-$, $OR^f$, $SR^f$, $(CHR^gCH_2O)_xR^f$, $(CH_2N(E^4))_xR^f$, $(CH_2CH_2N(E^4))_xR^f$, halogen, trifluoromethyl, nitro, acyl or cyano, where $R^f$, $E^4$, $E^5$ and $E^6$ are identical or different radicals selected from among hydrogen, alkyl, cycloalkyl and aryl, $R^g$ is hydrogen, methyl or ethyl, $M^+$ is a cation, $X^-$ is an anion and x is an integer from 1 to 120, or in each case two radicals $R^5$, $R^6$, $R^7$, $R^8$, $R^9$ and $R^{10}$ bound to adjacent carbon atoms of the benzene rings together with the two adjacent carbon atoms of the benzene ring to which they are bound form a fused ring system having 1, 2 or 3 further rings.

For the purposes of the present invention, the expression "alkyl" encompasses straight-chain and branched alkyl groups. They are preferably straight-chain or branched $C_1$–$C_{12}$-alkyl groups, more preferably $C_1$–$C_8$-alkyl groups and particularly preferably $C_1$–$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl.

Substituted alkyl radicals preferably bear 1, 2, 3, 4 or 5, in particular 1, 2 or 3, substituents selected from among cycloalkyl, aryl, hetaryl, halogen, $NE^1E^2$, $NE^1E^2E^{3+}$, carboxyl, carboxylate, —$SO_3H$ and sulfonate.

A cycloalkyl group is preferably a $C_5$–$C_7$-cycloalkyl group such as cyclopentyl, cyclohexyl or cycloheptyl.

If the cycloalkyl group is substituted, it preferably bears 1, 2, 3, 4 or 5, in particular 1, 2 or 3, substituents selected from among alkyl, alkoxy and halogen.

Aryl is preferably phenyl, tolyl, xylyl, mesityl, naphthyl, anthracenyl, phenanthrenyl, naphthacenyl, in particular phenyl or naphthyl.

Substituted aryl radicals preferably bear 1, 2, 3, 4 or 5, in particular 1, 2 or 3, substituents selected from among alkyl, alkoxy, carboxyl, carboxylate, trifluoromethyl, —$SO_3H$, sulfonate, $NE^1E^2$, alkylene-$NE^1E^2$, nitro, cyano and halogen.

Hetaryl is preferably pyrrolyl, pyrazolyl, imidazolyl, indolyl, carbazolyl, pyridyl, quinolinyl, acridinyl, pyridazinyl, pyrimidinyl or pyrazinyl.

Substituted hetaryl radicals preferably bear 1, 2 or 3 substituents selected from among alkyl, alkoxy, carboxyl, carboxylate, —SO$_3$H, sulfonate, NE$^1$E$^2$, alkylene-NE$^1$E$^2$, trifluoromethyl and halogen.

What has been said above in respect of alkyl, cycloalkyl and aryl radicals applies analogously to alkoxy, cycloalkyloxy and aryloxy radicals.

The radicals NE$^1$E$^2$, NE$^4$E$^5$, NE$^7$E$^8$ and NE$^9$E$^{10}$ are preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Halogen is fluorine, chlorine, bromine or iodine, preferably fluorine, chlorine or bromine.

For the purposes of the present invention carboxylate and sulfonate are preferably a derivative of a carboxylic acid function or a sulfonic acid function, in particular a metal carboxylate or sulfonate, a carboxylic or sulfonic ester function or a carboxamide or sulfonamide function. They include, for example, esters of C$_1$–C$_4$-alkanols such as methanol, ethanol, n-propanol, isopropanol, n-butanol, sec-butanol and tert-butanol.

M$^+$ is preferably an alkali metal cation such as Li$^+$, Na$^+$ or K$^+$, NH$_4^+$ or a quaternary ammonium compound as is obtainable by protonation or quaternization of amines.

X$^-$ is preferably halide, particularly preferably Cl$^-$ or Br$^-$.

x and y are each, independently of one another, preferably an integer from 2 to 100.

A$^1$ and A$^2$ are each, independently of one another, preferably O, S, SiR$^a$R$^b$, NR$^c$ and CR$^{11}$R$^{12}$, where R$^a$, R$^b$, R$^{11}$ and R$^{12}$ are each, independently of one another, hydrogen, C$_1$–C$_8$-alkyl, C$_5$–C$_8$-cycloalkyl, aryl or hetaryl. In particular, R$^a$, R$^b$, R$^{11}$ and R$^{12}$ are each, independently of one another, hydrogen or C$_1$–C$_4$-alkyl such as methyl, ethyl, n-propyl, n-butyl or tert-butyl. R$^a$ and R$^b$ are particularly preferably both methyl. R$^{11}$ and R$^{12}$ are also particularly preferably both methyl.

It is preferred that one of the radicals A$^1$ or A$^2$ is O or S and the other is CR$^{11}$R$^{12}$.

It is preferred that one of the radicals A$^1$ or A$^2$ is a single bond and the other is O, S, SiR$^a$R$^b$, NR$^c$ or CR$^{11}$R$^{12}$.

In a first preferred embodiment, the radicals R$^1$ and R$^2$ or R$^3$ and R$^4$ are not connected by a bridge. In this case, the radicals R$^1$ and R$^2$ and/or R$^3$ and R$^4$ are preferably selected from among substituted or unsubstituted cycloalkyl, substituted or unsubstituted aryl and substituted or unsubstituted hetaryl. The radicals R$^1$, R$^2$, R$^3$ and R$^4$ are each, independently of one another, preferably phenyl radicals which may bear one, two or three substituents selected from among alkyl, alkoxy, halogen, trifluoromethyl, nitro, cyano, alkoxycarbonyl and carboxyl.

In a further preferred embodiment, the radicals R$^1$ and R$^2$ or R$^3$ and R$^4$ are connected by a bridge. In that case, R$^1$ and R$^2$ and/or R$^3$ and R$^4$ together with the phosphorus atom to which they are bound preferably form a five- to eight-membered heterocycle which may additionally be fused with one, two or three cycloalkyl, heterocycloalkyl, aryl or hetaryl groups, where the heterocycle and, if present, the fused-on groups may each bear, independently of one another, one, two, three or four substituents selected from among alkyl, cycloalkyl, heterocycloalkyl, aryl, hetaryl, COOR$^d$, COO$^-$M$^+$, SO$_3$R$^d$, SO$^-_3$M$^+$, NE$^1$E$^2$, alkylene-NE$^1$E$^2$, NE$^1$E$^2$E$^{3+}$X$^-$, alkylene-NE$^1$E$^2$E$^{3+}$X$^-$, OR$^d$, SR$^d$, (CHR$^e$CH$_2$O)$_y$R$^d$, (CH$_2$N(E$^1$))$_y$R$^d$, (CH$_2$CH$_2$N(E$^1$))$_y$R$^d$, halogen, trifluoromethyl, nitro, acyl and cyano, where R$^d$, R$^e$, E$^1$, E$^2$, E$^3$, M$^+$, X$^-$ and y are as defined above.

Preference is given to the radicals R$^1$ and R$^2$ and/or R$^3$ and R$^4$ together with the phosphorus atom to which they are bound forming a phosphine radical of the formula II

(II)

where

D together with the phosphorus atom to which it is bound forms a 5- to 8-membered heterocycle which may be fused with one, two or three cycloalkyl, heterocycloalkyl, aryl and/or hetaryl groups, where the fused-on groups may each bear, independently of one another, one, two, three or four substituents selected from among alkyl, alkoxy, halogen, SO$_3$H, sulfonate, NE$^1$E$^2$, alkylene-NE$^1$E$^2$, nitro, cyano, carboxyl and carboxylate, and/or D may bear one, two or three substituents selected from among alkyl, alkoxy, substituted or unsubstituted cycloalkyl and substituted or unsubstituted aryl, and/or D may be interrupted by 1, 2 or 3 substituted or unsubstituted heteroatoms.

The radical D is preferably a C$_2$–C$_6$-alkylene bridge which may be fused with 1 or 2 aryl groups and/or may bear a substituent selected from among alkyl, substituted or unsubstituted cycloalkyl and substituted or unsubstituted aryl and/or may be interrupted by a substituted or unsubstituted heteroatom.

The fused-on aryls of the radicals D are preferably benzene or naphthalene. Fused-on benzene rings are preferably unsubstituted or bear 1, 2 or 3, in particular 1 or 2, substituents selected from among alkyl, alkoxy, halogen, SO$_3$H, sulfonate, NE$^7$E$^8$, alkylene-NE$^7$E$^8$, trifluoromethyl, nitro, carboxyl, alkoxycarbonyl, acyl and cyano. Fused-on naphthalenes are preferably unsubstituted or bear 1, 2 or 3, in particular 1 or 2, of the substituents mentioned above for the fused-on benzene rings on the ring which is not fused on and/or on the fused-on ring. In the case of the substituents on the fused-on aryls, alkyl is preferably C$_1$–C$_4$-alkyl and in particular methyl, isopropyl or tert-butyl. Alkoxy is preferably C$_1$–C$_4$-alkoxy and in particular methoxy. Alkoxycarbonyl is preferably C$_1$–C$_4$-alkoxycarbonyl. Halogen is particularly preferably fluorine or chlorine.

If the C$_2$–C$_6$-alkylene bridge of the radical D is interrupted by 1, 2 or 3 substituted or unsubstituted heteroatoms, these are preferably selected from among O, S, NR$^i$ and SiR$^i$R$^i$, where the radicals R$^i$ are each, independently of one another, alkyl, cycloalkyl or aryl. Preference is given to the C$_2$–C$_6$-alkylene bridge of the radical D being interrupted by a substituted or unsubstituted heteroatom.

If the C$_2$–C$_6$-alkylene bridge of the radical D is substituted, it preferably bears 1, 2 or 3 substituents, in particular 1 substituent, selected from among alkyl, cycloalkyl and aryl, where the aryl substituent may bear 1, 2 or 3 of the substituents mentioned for aryl. The alkylene bridge D preferably bears one substituent selected from among methyl, ethyl, isopropyl, phenyl, p-(C$_1$–C$_4$-alkyl) phenyl, preferably p-methylphenyl, p-(C$_1$–C$_4$-alkoxy) phenyl, preferably p-methoxyphenyl, p-halophenyl, preferably p-chlorophenyl, and p-trifluoromethylphenyl.

The radical D is preferably a C$_3$–C$_6$-alkylene bridge which may be fused and/or substituted and/or interrupted by substituted or unsubstituted heteroatoms as described above. In particular, the radical D is a C$_3$–C$_6$-alkylene bridge which is fused with one or two benzene and/or naphthalene groups, where the benzene or naphthalene groups may bear 1, 2 or 3, in particular 1 or 2, of the abovementioned substituents.

Preference is given to the radical D together with the phosphorus atom to which it is bound (i.e. the radicals $R^1$ and $R^2$ or $R^3$ and $R^4$ together with the phosphorus atom to which they are bound) forming a radical selected from among radicals of the formulae II.1 to II.4

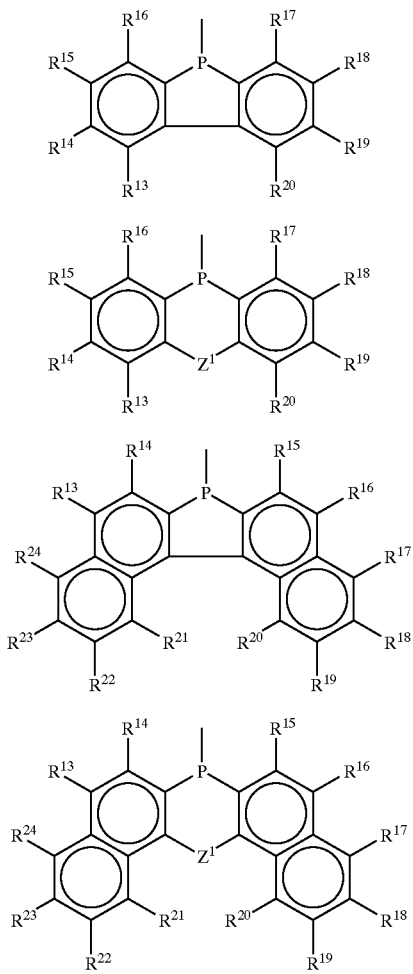

where
- $Z^1$ is O, S, $NR^i$ or $SiR^iR^i$, where
  - $R^i$ is alkyl, cycloalkyl or aryl, or
- $Z^1$ is a $C_1$–$C_3$-alkylene bridge which may contain a double bond and/or bear an alkyl, cycloalkyl or aryl substituent, where the aryl substituent may bear one, two or three of the substituents mentioned for aryl, or
- $Z^1$ is a $C_2$–$C_3$-alkylene bridge which is interrupted by O, S, $NR^i$ or $SiR^iR^i$,
- $R^{13}$, $R^{14}$, $R^{15}$, $R^{16}$, $R^{17}$, $R^{18}$, $R^{19}$ $R^{20}$, $R^{21}$, $R^{22}$, $R^{23}$ and $R^{24}$ are each, independently of one another, hydrogen, alkyl, cycloalkyl, aryl, alkoxy, halogen, $SO_3H$, sulfonate, $NE^7E^8$, alkylene-$NE^7E^8$, trifluoromethyl, nitro, alkoxycarbonyl, carboxyl or cyano, where $E^7$ and $E^8$ are each, independently of one another, hydrogen, alkyl, cycloalkyl or aryl.

D is preferably a radical of the formula II.1 in which $R^{13}$, $R^{14}$, $R^{15}$ and $R^{16}$ are each hydrogen.

D is preferably a radical of the formula II.2, in which $R^{13}$ $R^{14}$, $R^{15}$ and $R^{16}$ are each hydrogen.

The radical $Z^1$ in the formulae II.1 and II.4 is preferably O.

The radicals $R^5$, $R^6$, $R^7$, $R^8$, $R^9$ and $R^{10}$ in the compounds of the formula I are preferably selected from among hydrogen, alkyl, cycloalkyl, aryl and hetaryl. It is preferred that $R^5$, $R^7$, $R^8$ and $R^{10}$ are each hydrogen and $R^6$ and $R^9$ are each $C_1$–$C_4$-alkyl such as methyl, ethyl, n-propyl, n-butyl or tert-butyl.

Preference is given to at least one of the radicals $R^5$, $R^6$, $R^7$, $R^8$, $R^9$ and $R^{10}$ being a polar (hydrophilic) group, which then generally results in water-soluble catalysts. The polar groups are preferably selected from among $COOR^f$, $COO^-M^+$, $SO_3R^f$, $SO^-_3M^+$, $NE^4E^5$, alkylene-$NE^4E^5$, $NE^4E^5E^{6+}$ $X^-$, alkylene-$NE^4E^5E^{6+}X^-$, $OR^f$, $SR^f$, $(CHR^gCH_2O)_xR^f$ or $(CH_2CH_2N(E^4))_xR^f$, where $E^4$, $E^5$, $E^6$, $R^f$, $R^g$, $M^+$, $X^-$ and x are as defined above.

If two radicals selected from among $R^5$, $R^6$, $R^7R^8$, $R^9$ and $R^{10}$ which are bound to adjacent carbon atoms of the benzene rings form a fused-on ring system, this system is preferably a benzene or naphthalene unit. Fused-on benzene rings are preferably unsubstituted or bear 1, 2 or 3, in particular 1 or 2, substituents selected from among alkyl, alkoxy, halogen, $SO_3H$, sulfonate, $NE^4E^5$, alkylene-$NE^4E^5$, trifluoromethyl, nitro, carboxyl, alkoxycarbonyl, acyl and cyano. Fused-on naphthalenes are preferably unsubstituted or bear 1, 2 or 3, in particular 1 or 2, of the substituents mentioned above for the fused-on benzene rings on the ring which is not fused on and/or on the fused-on ring.

In a preferred embodiment of the process of the present invention, used is made of a hydroformylation catalyst in which the bidentate phosphine ligand of the formula I is selected from among compounds of the formulae I.1 to I.3

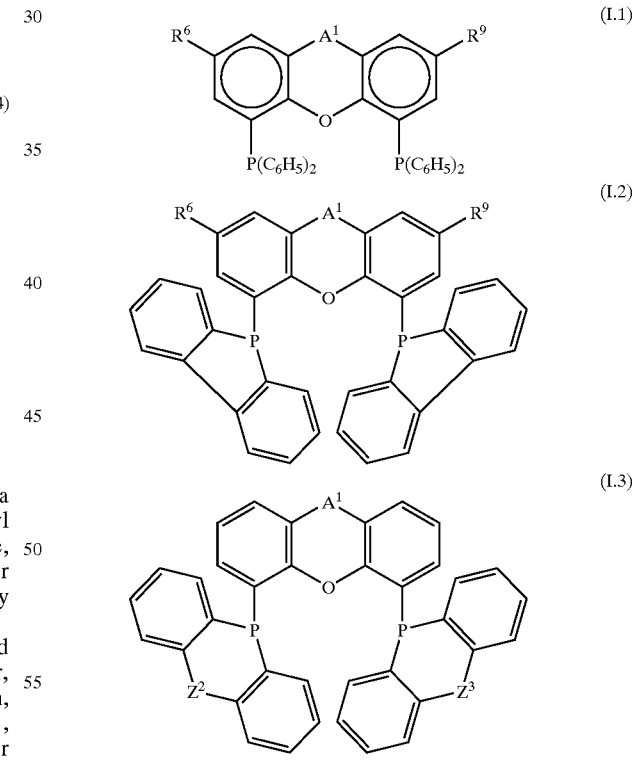

where
- $A^1$ is a single bond, O, S, $SiR^aR^b$, $NR^c$ or $CR^{11}R^{12}$, where $R^a$, $R^b$, $R^c$, $R^{11}$ and $R^{12}$ are each, independently of one another, hydrogen or $C_1$–$C_4$-alkyl,
- $Z^2$ and $Z^3$ are each, independently of one another, O, S, $NR^i$ $SiR^iR^i$ or $CR^iR^i$, where the radicals $R^i$ are each, independently of one another, alkyl, cycloalkyl or aryl, and $R^6$ and $R^9$ are each, independently of one another, hydrogen or $C_1$–$C_4$-alkyl.

The monodentate phosphine ligand is preferably selected from among trialkylphosphines such as triethylphosphine, tri-n-propyl-phosphine, triisopropylphosphine, tri-n-butylphosphine, tri-tert-butylphosphine, dialkylarylphosphines such as diethylphenylphosphine, alkyldiarylphosphines such as diphenylmethylphosphine and diphenylethylphosphine, triarylphosphines such as triphenylphosphine, tri(p-tolyl)-phosphine, tricycloalkylphosphines such as tricyclohexylphosphine and mixtures thereof. Preference is given to using triarylphosphines, in particular triphenylphosphine.

The catalysts used according to the present invention may comprise one or more monodentate phosphine ligands and one or more bidentate phosphine ligands.

In addition to the above-described ligands, at least one further ligand selected from among halides, amines, carboxylates, acetylacetonate, arylsulfonates and alkylsulfonates, hydride, CO, olefins, dienes, cycloolefins, nitriles, N-containing heterocycles, aromatics and heteroaromatics, ethers, $PF_3$, phospholes, phosphabenzenes and monodentate, bidentate and polydentate phosphinite, phosphonite, phosphoramidite and phosphite ligands may also be present in the catalysts.

The metal of transition group VIII is preferably cobalt, ruthenium, rhodium, palladium, platinum, osmium or iridium, in particular cobalt, rhodium, ruthenium or iridium.

The compounds of the formula I used according to the present invention can be prepared, for example, starting from a compound of the formula I.a

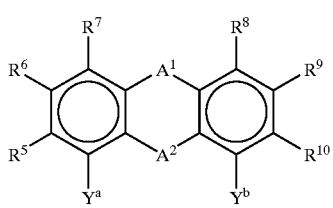

(I.a)

where $Y^a$ and $Y^b$ are each, independently of one another, halogen, OH, $OC(O)CF_3$ or $SO_3Me$ where Me=hydrogen, Li, Na or K, where $Y^a$ and/or $Y^b$ can also be hydrogen when at least one of the radicals $R^5$ and $R^{10}$ is hydrogen, an alkoxy group or an alkoxycarbonyl group which is located in the ortho position relative to $Y^a$ and/or $Y^b$, and $A^1$, $A^2$, $R^5$, $R^6$, $R^7$, $R^8$, $R^9$ and $R^{10}$ are as defined above.

The functionalization of the radicals $Y^a$ and $Y^b$ to form the radicals $PR^1R^2$ and $PR^3R^4$ can be carried out by procedures analogous to known methods. For example, it is possible firstly to lithiate compounds of the formula I.a in which $Y^a$ and $Y^b$ are each halogen, preferably chlorine or bromine, and to react the intermediate formed with a compound bearing a halogen atom, preferably a chlorine atom, on the phosphorus atom, for example a compound of the formula Cl—$PR^1R^2$ and/or Cl—$PR^3R^4$.

In place of compounds of the formula I.a in which $Y^a$=$Y^b$=halogen, it is also possible to lithiate compounds I.a in which $Y^a$=$Y^b$=hydrogen and in which hydrogen, an alkoxy group or an alkoxycarbonyl group is located in each of the ortho positions relative to $Y^a$ and $Y^b$. Such reactions are described in the literature as "ortho-lithiation" (cf. for example, D. W. Slocum, J. Org. Chem., 1976, 41, 3652–3654; J. M. Mallan, R. L. Bebb, Chem. Rev., 1969, 693 ff; V. Snieckus, Chem. Rev., 1980, 6, 879–933). The organolithium compounds obtained can then be reacted in the above-described manner with the phosphorus-halogen compounds to form the target compounds I.

In general, the catalysts or catalyst precursors used in each case are converted under hydroformylation conditions into catalytically active species of the formula $H_xM_y(CO)_q L'_rL''_s$, where M is a metal of transition group VIII, $L'$ is a monodentate phosphine ligand, $L''$ is a bidentate phosphine ligand of the formula I and x, y, q, r and s are integers which depend on the valence and type of the metal and on the number of coordination sites occupied by the ligand, with r also being able to be 0. q, r and s are each, independently of one another, preferably a positive integer, e.g. 1, 2 or 3. The sum of q, r and s is preferably from 2 to 5. If desired, the complexes can further comprise at least one of the above-described additional ligands. In the catalyst systems used according to the present invention, it is also not absolutely necessary for a monodentate phosphine ligand complex to be present in the catalytically active species, as long as the catalyst system used comprises at least one such ligand.

In a preferred embodiment, the hydroformylation catalysts are prepared in situ in the reactor used for the hydroformylation reaction. However, if desired, the catlysts used according to the present invention can also be prepared separately and isolated by customary methods. For the in situ preparation of the catalysts used according to the present invention, it is possible, for example, to react at least one monodentate phosphine ligand, at least one compound of the formula I, a compound or a complex of a metal of transition group VIII, if desired at least one additional ligand and, if desired, an activating agent in an inert solvent under the hydroformylation conditions.

Suitable rhodium compounds or complexes are, for example, rhodium(II) and rhodium(III) salts such as rhodium(III) chloride, rhodium(III) nitrate, rhodium(III) sulfate, potassium-rhodium sulfate, rhodium(II) and rhodium(III) carboxylates, rhodium(II) and rhodium(III) acetate, rhodium(III) oxide, salts of rhodic(III) acid, trisammonium hexachlororhodate(III), etc. Rhodium complexes such as dicarbonylrhodium acetylacetonate, acetylacetonatobisethylenerhodium(I), rhodiummethylhexanoate, etc., are also suitable. Preference is given to using dicarbonylrhodium acetylacetonate or rhodium acetate.

Ruthenium salts or compounds can likewise be used. Suitable ruthenium salts are, for example, ruthenium(III) chloride, ruthenium(IV), ruthenium(VI) and ruthenium (VIII) oxides, alkali metal salts of ruthenium oxo acids, e.g. $K_2RuO_4$ or $KRuO_4$, or complexes such as $RuHCl(CO)(PPh_3)_3$. It is also possible to use carbonyls of ruthenium, e.g. dodecacarbonyltriruthenium or octadecacarbonylhexaruthenium, or mixed forms in which CO is partly replaced by ligands of the formula $PR_3$, e.g. $Ru(CO)_3(PPh_3)_2$, in the process of the present invention.

Suitable cobalt compounds are, for example, cobalt(II) chloride, cobalt(II) sulfate, cobalt(II) carbonate, cobalt(II) nitrate, their amine or hydrate complexes, cobalt carboxylates such as cobalt acetate, cobalt ethylhexanoate, cobalt naphthanoate, and also the cobalt-caprolactamate complex. Here too, carbonyl complexes of cobalt, e.g. octacarbonyldicobalt, dodecacarbonyltetracobalt and hexadecacarbonylhexacobalt, can be used.

The abovementioned and further suitable compounds of cobalt, rhodium, ruthenium and iridium are known in principle and are adequately described in the literature or they can be prepared by a person skilled in the art using methods analogous to those for the known compounds.

Suitable activating agents are, for example, Brönsted acids, Lewis acids, e.g. $BF_3$, $AlCl_3$, $ZnCl_2$, and Lewis bases.

As solvents, preference is given to using the aldehydes which are formed in the hydroformylation of the respective olefins and also their higher-boiling downstream reaction products, e.g. the products of aldol condensation. Further solvents which can likewise be used are aromatics such as toluene and xylenes, hydrocarbons and mixtures of hydrocarbons; these can also be used for dilution of the above-mentioned aldehydes and the downstream products of the aldehydes. Further suitable solvents are esters of aliphatic carboxylic acids with alkanols, for example, ethyl acetate or Texanol™, ethers such as tert-butyl methyl ether and tetrahydrofuran. In the case of sufficiently hydrophilic ligands, it is also possible to use alcohols such as methanol, ethanol, n-propanol, isopropanol, n-butanol, isobutanol, ketones such as acetone and methyl ethyl ketone, etc. Furthermore, "ionic liquids" can also be used as solvents. These are liquid salts, for example N,N'-dialkylimidazolium salts such as N-butyl-N'-methylimidazolium salts, tetraalkylammonium salts such as tetra-n-butylammonium salts, N-alkylpyridinium salts such as N-butylpyridinium salts, tetraalkylphosphonium salts such as trishexyl(tetradecyl)phosphonium salts, e.g. the tetrafluoro-borates, acetates, tetrachloroaluminates, hexafluorophosphates, chlorides and tosylates.

It is also possible to carry out the reactions in water or aqueous solvent systems comprising water together with a water-miscible solvent, for example an alcohol such as methanol, ethanol, n-propanol, isopropanol, n-butanol, isobutanol, a ketone such as acetone or methyl ethyl ketone or another solvent. For this purpose, preference is given to using ligands of the formula I which are modified with polar groups, for example ionic groups such as $SO_3Me$, $CO_2Me$ where Me=Na, K or $NH_4$ or $N(CH_3)_3^+$. The reactions then occur as a two-phase catalysis in which the catalyst is present in the aqueous phase and starting materials and products form the organic phase. The reaction in the "ionic liquids" can also be carried out as a two-phase catalysis.

The molar ratio of phosphorus-containing ligands to metal of transition group VIII is generally in a range from about 1:1 to 1 000:1.

Substrates which can be used in the hydroformylation process of the present invention are in principle all compounds which contain one or more ethylenically unsaturated double bonds. They include, for example, olefins such as α-olefins, internal straight-chain and internal branched olefins. Suitable α-olefins are, for example, ethylene, propene, 1-butene, 1-pentene, 1-hexene, 1-heptene, 1-octene, 1-nonene, 1-decene, 1-undecene, 1-dodecene, etc.

Preferred branched, internal olefins are $C_4–C_{20}$-olefins such as 2-methyl-2-butene, 2-methyl-2-pentene, 3-methyl-2-pentene, branched, internal heptene mixtures, branched, internal octene mixtures, branched, internal nonene mixtures, branched, internal decene mixtures, branched, internal undecene mixtures, branched, internal dodecene mixtures, etc.

Further olefins suitable for the hydroformylation process are $C_5–C_8$-cycloalkenes such as cyclopentene, cyclohexene, cycloheptene, cyclooctene and derivatives thereof, e.g. their $C_1–C_{20}$-alkyl derivatives having from 1 to 5 alkyl substituents. In addition, vinylaromatics such as styrene, α-methylstyrene, 4-isobutylstyrene, etc., can also be hydroformylated. Further suitable olefins for the hydroformylation reaction are α,β-ethylenically unsaturated monocarboxylic and/or dicarboxylic acids, their esters, monoesters and amides, e.g. acrylic acid, methacrylic acid, maleic acid, fumaric acid, crotonic acid, itaconic acid, methyl 3-pentenoate, methyl 4-pentenoate, methyl oleate, methyl acrylate, methyl methacrylate, unsaturated nitriles such as 3-pentenenitrile, 4-pentenenitrile, acrylonitrile, vinyl ethers such as vinyl methyl ether, vinyl ethyl ether, vinyl propyl ether, etc., $C_1–C_{20}$-alkenols, -alkenediols and -alkadienols, e.g. 2,7-octadien-1-ol. Further suitable substrates are dienes or polyenes having isolated or conjugated double bonds. These include, for example, 1,3-butadiene, 1,4-pentadiene, 1,5-hexadiene, 1,6-heptadiene, 1,7-octadiene, vinylcyclohexene, dicyclopentadiene, 1,5,9-cyclooctatriene and also homopolymers and copolymers of butadiene.

The unsaturated compound used for the hydroformylation is preferably selected from among internal linear olefins and olefin mixtures in which at least one internal linear olefin is present. Preferred linear (straight-chain) internal olefins are $C_4–C_{20}$-olefins such as 2-butene, 2-pentene, 2-hexene, 3-hexene, 2-heptene, 3-heptene, 2-octene, 3-octene, 4-octene, etc. and mixtures thereof.

The hydroformylation process of the present invention is preferably carried out using an industrially available olefin mixture which comprises, in particular, at least one internal linear olefin. Such mixtures include, for example, the Ziegler olefins obtained by targeted ethene oligomerization in the presence of alkylaluminum catalysts. These are essentially unbranched olefins having a terminal double bond and an even number of carbon atoms. Suitable olefin mixtures also include the olefins obtained by ethene oligomerization in the presence of various catalyst systems, e.g. the predominantly linear α-olefins obtained in the presence of alkylaluminum chloride/titanium tetrachloride catalysts and the α-olefins obtained in the presence of nickel-phosphine complexes as catalysts by means of the Shell Higher Olefin Process (SHOP). Suitable industrially available olefin mixtures are also obtained in the dehydrogenation of appropriate petroleum fractions, e.g. kerosene or diesel oil fractions. The conversion of paraffins, predominantly n-paraffins, into olefins is carried out using essentially three methods:

thermal cracking (steam cracking),
catalytic dehydrogenation and
chemical dehydrogenation by chlorination and dehydrochlorination.

Thermal cracking leads predominantly to α-olefins, while the other variants produce olefin mixtures which generally have relatively large proportions of olefins containing an internal double bond. Suitable olefin mixtures also include the olefins obtained in metathesis or telomerization reactions. They include, for example, the olefins from the Phillips triolefin process, a modified SHOP process, comprising ethylene oligomerization, double bond isomerization and subsequent metathesis (ethenolysis).

Further industrial olefin mixtures which can be used in the hydroformylation process of the present invention are selected from among dibutenes, tributenes, tetrabutenes, dipropenes, tripropenes, tetrapropenes, mixtures of butene isomers, in particular raffinate II, dihexenes, dimers and oligomers from the Dimersol® process of IFP, the Octol® process of Hüls, the Polygas process, etc.

Preference is given to using 1-butene-containing hydrocarbon mixtures. These include, in particular, raffinate II. Suitable 1-butene-containing hydrocarbon mixtures may contain a proportion of saturated hydrocarbons. Mixtures having a low proportion of high-boiling components are advantageous.

The hydroformylation reaction in the process of the present invention can be carried out continuously, semicontinuously or batchwise. The advantages of the process of the present invention are especially evident when the process is carried out semicontinuously or, in particular, continuously. The invention provides a process which comprises (i) reacting the compound(s) containing at least one ethylenically unsaturated double bond in a reaction zone in the presence of carbon monoxide, hydrogen and the catalyst system, (ii) taking an output from the reaction zone and separating it into a fraction enriched in product and a fraction enriched in catalyst system, (iii) if desired, subjecting the fraction enriched in catalyst system obtained in step (ii) to work-up and (iv) returning at least part of the fraction enriched in catalyst system, if desired after work-up, to the reaction zone, where at least one of these steps (ii) to (iv) is carried out essentially in the absence of carbon monoxide and hydrogen and in the presence of at least one monodentate phosphine ligand.

In a first preferred embodiment, the steps (i) to (iv) are all carried out in the presence of at least one monodentate phosphine ligand.

In a second preferred embodiment, only some of the steps (i) to (iv) are carried out in the presence of a monodentate phosphine ligand. According to the present invention, the presence of monodentate phosphine ligands in reaction steps carried out in the absence of carbon monoxide and hydrogen is absolutely necessary.

Step (i)

Reactors suitable for a continuous reaction are known to those skilled in the art and are described, for example, in Ullmanns Enzyklopädie der technischen Chemie, vol. 1, 3rd edition, 1951, p. 743 ff.

Suitable pressure-rated reactors are likewise known to those skilled in the art and are described, for example, in Ullmanns Enzyklopädie der technischen Chemie, vol. 1, 3rd edition, 1951, p. 769 ff. In general, the process of the present invention is carried out using an autoclave which may, if desired, be provided with a stirrer and an internal lining.

The composition of the synthesis gas comprising carbon monoxide and hydrogen used in step (i) of the process of the present invention can vary within a wide range. The molar ratio of carbon monoxide to hydrogen is generally from about 5:95 to 70:30, preferably from about 40:60 to 60:40. Particular preference is given to using a molar ratio of carbon monoxide to hydrogen in the region of 1:1.

The temperature in the hydroformylation reaction is generally in a range from about 20 to 180° C., preferably from about 50 to 150° C. The reaction is generally carried out at the partial pressure of the reaction gas at the reaction temperature selected. In general, the pressure is in a range from about 1 to 700 bar, preferably from 1 to 600 bar, in particular from 1 to 300 bar. The reaction pressure can be varied as a function of the activity of the hydroformylation catalyst used in the process of the present invention. In general, the catalysts used according to the present invention permit a reaction in a low pressure range, for instance in the range from 0.1 to 100 bar.

Step (ii)

The separation of the output taken from the reaction zone into a fraction enriched in product and a fraction enriched in catalyst system is carried out by customary methods known to those skilled in the art. Preference is given to distillation using known separation apparatuses such as distillation columns, e.g. tray columns which may, if desired, be equipped with bubble caps, sieve plates, sieve trays, valves, etc., and evaporators, e.g. thin film evaporators, falling film evaporators, wiped film evaporators, etc.

In a useful embodiment of the process of the present invention, step (i) is carried out in the absence of a monodentate phosphine ligand and step (ii) is carried out in the presence of at least one monodentate phosphine ligand. The monodentate phosphine ligand can, for example, be added to the output from the reaction zone.

Step (iii)

The fraction enriched in catalyst system can be subjected to one or more work-up steps before it is returned to the hydroformylation process. Such steps include, for example, purification steps for the partial or complete removal of high-boiling products of the hydroformylation reaction. Suitable purification processes are, for example, membrane filtration, isolation of the catalyst, e.g. by precipitation of a catalyst-cocatalyst complex, injection of steam to achieve partial or complete removal of high-boiling by-products, etc.

Step (iv)

All or some of the fraction enriched in catalyst system is, if desired after work-up as described above, fed into the reaction zone and thus returned to the hydroformylation process. If the hydroformylation stage comprises more than one reactor, all or some of the fraction enriched in catalyst system can be fed into each of the reactors. If desired, the monodentate phosphine ligand can be separated off by customary methods known to those skilled in the art before the fraction enriched in catalyst system is returned to the reaction zone.

It is advantageous for the catalyst systems used according to the present invention and the catalytically active species formed therefrom under the hydroformylation conditions to be stable in the absence of CO and $H_2$ (synthesis gas), too. The disadvantages observed according to the prior art in the case of hydroformylation catalysts based on bidentate phosphine ligands and especially those having a xanthene skeleton, for example irreversible decomposition or a pronounced tendency to crystallize in the absence of CO and $H_2$, generally do not occur. The catalysts used according to the present invention thus have long catalyst operating lives and are also suitable for continuous hydroformylation processes. The latter can advantageously comprise one or more process steps such as the separation of reaction products and the work-up of catalyst-containing fractions which are carried out in the absence of CO and $H_2$.

Surprisingly, the catalysts used according to the present invention generally display a selectivity which is as good as or better than corresponding catalysts from the prior art which contain no monodentate phosphine ligand. Thus, the catalyst systems used according to the present invention advantageously display a high selectivity to α-aldehydes or α-alcohols in the hydroformylation of α-olefins. In general, good yields of n-aldehydes or n-alcohols are generally also obtained. Surprisingly, it is generally also possible to stabilize higher rhodium concentrations by use of a monodentate phosphine ligand in the catalyst systems than is the case for catalysts from the prior art.

Catalysts of the above-described type which comprise chiral compounds of the formula I are suitable for enantioselective hydroformylation.

The above-described catalysts can also be immobilized on a suitable support, e.g. glass, silica gel, synthetic resins, etc., by suitable methods, e.g. by bonding via functional groups suitable as anchor groups, adsorption, grafting, etc. They are then also suitable for use as solid phase catalysts.

The invention is illustrated by the nonrestrictive examples below.

EXAMPLES

General Experimental Procedure for Carrying Out the Hydroformylation Experiments:

Rhodium precursor, bidentate phosphine ligand, monodentate phosphine ligand (in the case of examples according to the present invention) and solvent were mixed under a nitrogen atmosphere in a Schlenk tube. The solution obtained in this way was transferred to a 100 ml autoclave which had been flushed with $CO/H_2$ (1:1). The autoclave was pressurized at room temperature with 5 bar of $CO/H_2$ (1:1). While stirring vigorously by means of a sparging stirrer, the reaction mixture was heated to the desired temperature over a period of 30 minutes. The olefin to be hydroformylated was then injected into the autoclave via a lock by means of $CO/H_2$ pressure. The desired reaction pressure was then set immediately by means of $CO/H_2$. This pressure was kept constant during the reaction by introduction of further synthesis gas via a pressure regulator. After the desired reaction time had elapsed, the autoclave was cooled, vented and emptied. The reaction mixtures were analyzed by means of gas chromatography (GC) using correction factors.

Comparative Example 1a
Low-Pressure Hydroformylation of 1-Octene

Use of 3.4 mg (0.013 mmol) of dicarbonylrhodium acetylacetonate, 38 mg (0.66 mmol) of 9,9-dimethyl-4,6-bis(diphenylphosphino)-xanthene, 11.8 g (105 mmol) of 1-octene (purity: 95%, balance: n-octenes having an internal double bond) and 10.8 g of Palatinol AH® (2-ethylhexyl ester of phthalic acid from BASF AG) in the general experimental procedure at 90° C., a synthesis gas pressure of 10 bar and a reaction time of 4 hours gave a 1-octene conversion of 58%. The yield of nonanals was 52%, the selectivity to n-nonanal (proportion of n-product) was 98% and the selectivity to n-nonanal and 2-methyloctanal (proportion of α-products) was 100%.

Comparative Example 1b
Low-Pressure Hydroformylation Using Recycled Catalyst from Comparative Example 1a The product aldehydes were distilled off from the crude reaction mixture obtained from comparative example 1a at about 100° C. under reduced pressure to leave a homogeneous, light-yellow solution comprising the catalyst system, Palatinol AH® and high boilers formed as by-products in the hydroformylation. To simulate long-term stress on the catalyst system, as occurs in a continuous process carried out over a prolonged period, this solution was stirred at 110° C. under a nitrogen atmosphere for 24 hours. During this time, the color of the solution slowly changed from light yellow to light brown. Precipitation of a dark brown solid also occurred. This solution was used for another hydroformylation under the conditions of the general experimental procedure. Reaction of 11.8 g (105 mmol) of 1-octene at 90° C., a synthesis gas pressure of 10 bar and a reaction time of 4 hours gave a 1-octene conversion of 56%. The yield of nonanals was 12%, the selectivity to n-nonanal (proportion of n-product) was 95% and the selectivity to n-nonanal and 2-methyloctanal (proportion of α-products) was 100%.

Example 1a (According to the Present Invention)
Low-Pressure Hydroformylation of 1-Octene Use of 3.6 mg (0.014 mmol) of dicarbonylrhodium acetylacetonate, 37 mg (0.065 mmol) of 9,9-dimethyl-4,6-bis(diphenylphosphino)-xanthene, 75 mg (0.286 mmol) of triphenylphosphine, 11.3 g (101 mmol) of 1-octene (purity: 95%, balance: n-octenes having an internal double bond) and 11.3 g of Palatinol AH® in the general experimental procedure at 90° C., a synthesis gas pressure of 10 bar and a reaction time of 4 hours gave a 1-octene conversion of 67%. The yield of nonanals was 61%, the selectivity to n-nonanal (proportion of n-product) was 98% and the selectivity to n-nonanal and 2-methyloctanal (proportion of α-products) was 100%.

Example 1b (According to the Present Invention)
Low-Pressure Hydroformylation with Recycling of the Catalyst System from Example 1a The product aldehydes were separated from the crude reaction mixture obtained from example 1a by distillation at 100° C. under reduced pressure. This left a homogeneous, light-yellow solution comprising the catalyst system, Palatinol® and high boilers formed in the hydroformylation reaction. To simulate long-term stress, the solution was stirred at 110° C. under a nitrogen atmosphere for 24 hours, and the color of the solution remained unchanged over this period. The solution was subsequently used again in a hydroformylation carried out using the general experimental procedure. Reaction of 11.6 g (103 mmol) of 1-octene at 90° C., a synthesis gas pressure of 10 bar and a reaction time of 4 hours gave a 1-octene conversion of 64%. The yield of nonanals was 58%, the selectivity to n-nonanal (proportion of n-product) was 98% and the selectivity to n-nonanal and 2-methyloctanal (proportion of α-products) was 100%.

Example 2a (According to the Present Invention)
Low-Pressure Hydroformylation of 1-Octene Use of 24 mg (0.093 mmol) of dicarbonylrhodium acetylacetonate, 257 mg (0.444 mmol) of 9,9-dimethyl-4,6-bis(diphenylphosphino)-xanthene, 469 mg (1.79 mmol) of triphenylphosphine, 16.0 g (143 mmol) of 1-octene (purity: 95%, balance: n-octenes having an internal double bond) and 17.5 g of Palatinol® in the general experimental procedure at 90° C., a synthesis gas pressure of 10 bar and a reaction time of 4 hours gave a 1-octene conversion of 93%. The yield of nonanals was 86%, the selectivity to n-nonanal (proportion of n-product) was 98% and the selectivity to n-nonanal and 2-methyloctanal (proportion of α-products) was 100%.

Example 2b (According to the Present Invention)
Low-Pressure Hydroformylation with Recycling of the Catalyst System from Example 2a The product aldehydes were separated from the crude reaction mixture obtained from example 2a by distillation at 100° C. under reduced pressure. This left a homogeneous, light-yellow solution comprising the catalyst system, Palatinol AH® and high boilers formed in the hydroformylation reaction. To simulate long-term stress, the solution obtained was stirred at 110° C. under a nitrogen atmosphere for 72 hours, and the color of the solution remained unchanged over this period. The solution was subsequently used for another hydroformylation under the conditions of the general experimental procedure. Reaction of 16.7 g (149 mmol) of 1-octene at 90° C., a synthesis gas pressure of 10 bar and a reaction time of 4 hours gave a 1-octene conversion of 96%. The yield of nonanals was 88%, the selectivity to n-nonanal (proportion of n-product) was 97% and the selectivity to n-nonanal and 2-methyloctanal (proportion of α-products) was 100%.

Example 3

Low-Pressure Hydroformylation of 1-Octene

Use of 3.8 mg (0.015 mmol) of dicarbonylrhodium acetylacetonate, 44 mg (0.076 mmol) of 9,9-dimethyl-4,6-bis(diphenylphosphino)-xanthene, 21 mg (0.105 mmol) of tributylphosphine, 15.0 g (134 mmol) of 1-octene and 15.0 g of Palatinol AH® in the general experimental procedure at 90° C., a synthesis gas pressure of 10 bar and a reaction time of 4 hours gave a 1-octene conversion of 56%. The yield of nonanals was 52%, the selectivity to n-nonanal (proportion of n-product) was 92% and the selectivity to n-nonanal and 2-methyloctanal (proportion of α-products) was 100%.

We claim:

1. A process for the hydroformylation of compounds containing at least one ethylenically unsaturated double bond by reaction with carbon monoxide and hydrogen in the presence of a catalyst system comprising at least one metal of transition group VIII and at least one bidentate phosphine ligand, which comprises (i) reacting the compound(s) containing at least one ethylenically unsaturated double bond in a reaction zone in the presence of carbon monoxide, hydrogen and the catalyst system, (ii) taking an output from the reaction zone and separating it into a fraction enriched in product and a fraction enriched in catalyst system, (iii) if desired, subjecting the fraction enriched in catalyst system obtained in step (ii) to work-up and (iv) returning at least part of the fraction enriched in catalyst system, if desired after work-up, to the reaction zone, where at least one of the steps (ii) to (iv) is carried out essentially in the absence of carbon monoxide and hydrogen and in the presence of at least one monodentate phosphine ligand.

2. A process as claimed in claim 1, wherein the bidentate phosphine ligand is selected from among compounds of the formula I

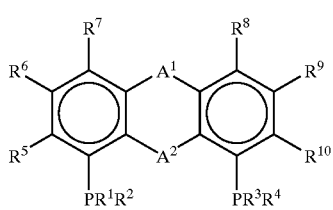

(I)

where $A^1$ and $A^2$ are each, independently of one another a single bond, O, S, $SiR^aR^b$, $NR^c$ or $CR^{11}R^{12}$, where $R^a$, $R^b$, $R^c$, $R^{11}$ and $R^{12}$ are each, independently of one another, hydrogen, alkyl, cycloalkyl, heterocycloalkyl, aryl or hetaryl, $R^1$, $R^2$, $R^3$ and $R^4$ are each, independently of one another, alkyl, cycloalkyl, heterocycloalkyl, aryl or hetaryl, which may each bear one, two or three substituents selected from among alkyl, cycloalkyl, heterocycloalkyl, aryl, hetaryl, $COOR^d$, $COO^-M^+$, $SO_3R^d$, $SO^-_3M^+$, $NE^1E^2$, alkylene-$NE^1E^2$, $NE^1E^2E^{3+}X^-$, alkylene-$NE^1E^2E^{3+}X^-$, $OR^d$, $SR^d$, $(CHR^eCH_2O)_yR^d$, $(CH_2N(E^1))_yR^d$, $(CH_2CH_2N(E^1))_yR^d$, halogen, trifluoromethyl, nitro, acyl and cyano where $R^d$, $E^1$, $E^2$ and $E^3$ are identical or different radicals selected from among hydrogen, alkyl, cycloalkyl and aryl, $R^e$ is hydrogen, methyl or ethyl, $M^+$ is a cation, $X^-$ is an anion and y is an integer from 1 to 120, or $R^1$ and $R^2$ and/or $R^3$ and $R^4$ together with the phosphorus atom to which they are bound form a 5- to 8-membered heterocycle which may additionally be fused with one, two or three cycloalkyl, heterocycloalkyl, aryl or hetaryl groups, where the heterocycle and, if present, the fused-on groups may each bear, independently of one another, one, two, three or four substituents selected from among alkyl, cycloalkyl, heterocycloalkyl, aryl, hetaryl, $COOR^d$, $COO^-M^+$, $SO_3R^d$, $SO^-_3M^+$, $NE^1E^2$, alkylene-$NE^1E^2$, $NE^1E^2E^{3+}X^-$, alkylene-$NE^1E^2E^{3+}X^-$, $OR^d$, $SR^d$, $(CHR^eCH_2O)_yR^d$, $(CH_2N(E^1))_yR^d$, $(CH_2CH_2N(E^1))_yR^d$, halogen, trifluoromethyl, nitro, acyl and cyano, where $R^d$, $R^e$, $E^1$, $E^2$, $E^3$, $M^+$, $X^{31}$, und y are as defined above, $R^5$, $R^6$, $R^7$, $R^8$, $R^9$ and $R^{10}$ are each, independently of one another, hydrogen, alkyl, cycloalkyl, heterocycloalkyl, aryl, hetaryl, $COOR^f$, $COO^-M^+$, $SO_3R^f$, $SO^-_3M^+$, $NE^4E^5$, $NE^4E^5E^{6+}X^-$, alkylene-$NE^4E^5E^{6+}X^-$, $OR^f$, $SR^f$, $(CHR^gCH_2O)_xR^f$, $(CH_2N(E^4))_xR^f$, $(CH_2CH_2N(E^4))_xR^f$, halogen, trifluoromethyl, nitro, acyl or cyano, where $R^f$, $E^4$, $E^5$ and $E^6$ are identical or different radicals selected from among hydrogen, alkyl, cycloalkyl and aryl, $R^g$ is hydrogen, methyl or ethyl, $M^+$ is a cation, $X^-$ is an anion and x is an integer from 1 to 120, or in each case two radicals $R^5$, $R^6$, $R^7$, $R^8$, $R^9$ and $R^{10}$ bound to adjacent carbon atoms of the benzene rings together with the two adjacent carbon atoms of the benzene ring to which they are bound form a fused ring system having 1, 2 or 3 further rings.

3. A process as claimed in claim 2, wherein the radicals $R^1$, $R^2$, $R^3$ and $R^4$ are, independently of one another, phenyl radicals which may bear 1, 2 or 3 substituents selected from among alkyl, alkoxy, halogen, trifluoromethyl, nitro, cyano, alkoxycarbonyl and carboxyl.

4. A process as claimed in claim 2, wherein the Radical $R^1$, $R^2$ and/or $R^3$ and $R^4$ together with the phosphorus atom to which they are bound form a radical selected from among radicals of the formulae II.1 to II.4,

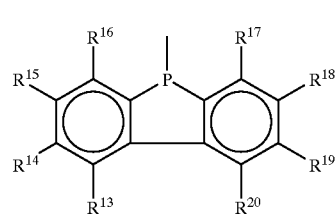

(II.1)

-continued

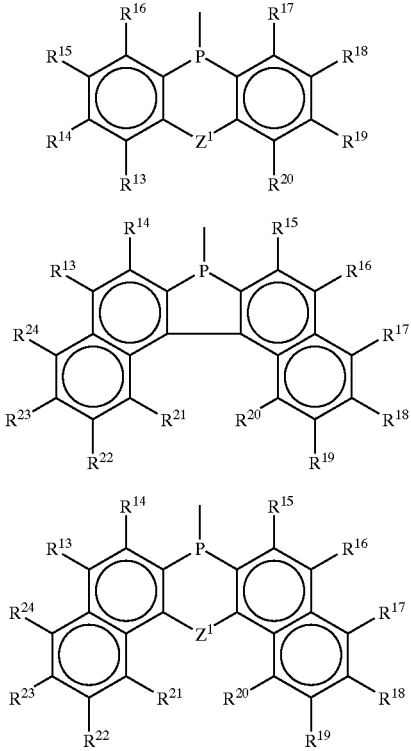

(II.2)

(II.3)

(II.4)

where

Z$^1$ is O, S, NR$^i$ or SiR$^i$R$^i$, where
R$^i$ is alkyl, cycloalkyl or aryl, or
Z$^1$ is a C$_1$–C$_3$-alkylene bridge which may contain a double bond and/or bear an alkyl, cycloalkyl or aryl substituent, where the aryl substituent may bear one, two or three of the substituents mentioned for aryl, or
Z$^1$ is a C$_2$–C$_3$-alkylene bridge which is interrupted by O, S, NR$^i$ or SiR$^i$R$^i$, R$^{13}$, R$^{14}$, R$^{15}$, R$^{16}$, R$^{17}$, R$^{18}$, R$^{19}$, R$^{20}$, R$^{21}$, R$^{22}$, R$^{23}$ and R$^{24}$ are each, independently of one another, hydrogen, alkyl cycloalkyl, aryl, alkoxy, halogen, SO$_3$H, sulfonate, NE$^7$E$^8$, alkylene-NE$^7$E$^8$, trifluoromethyl, nitro, alkoxycarbonyl, carboxyl or cyano, where E$^7$ and E$^8$ are each, independently of one anther, hydrogen, alkyl, cycloalkyl or aryl.

5. A process as claimed in claim 1, wherein the compound of the formula I is selected from among compounds of the formulae I.1 to I.3,

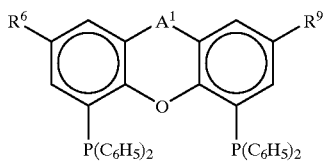

(I.1)

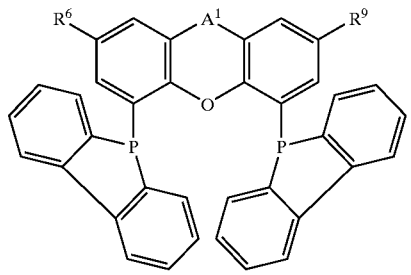

(I.2)

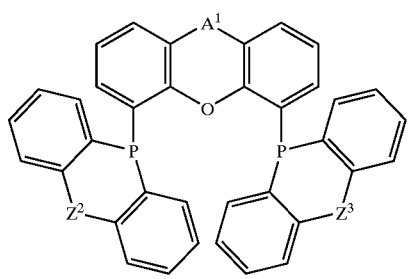

(I.3)

where

A$^1$ is a singel bond, O, S, SiR$^a$R$^b$, NR$^c$ or CR$^{11}$R$^{12}$, where R$^a$, R$^b$, R$^c$, R$^{11}$ and R$^{12}$ are each, independently of one another, hydrogen or C$_1$–C$_4$-alkyl, Z$^2$ and Z$^3$ are each, independently of one another, O, S, NR$^i$SiR$^i$R$^i$ or CR$^i$R$^i$, Where R$^i$ is alkyl, cycloalkyl or aryl, and R$^6$ and R$^9$ are each, independently of one another, hydrogen or C$_1$–C$_4$-alkyl.

6. A process as claimed in claim 1, wherein the monodentate phosphine ligand is selected from among compounds of the formula PR$^{21}$R$^{22}$R$^{23}$, where R$^{21}$, R$^{22}$ and R$^{23}$ are each, independently of one another, alkyl, cycloalkyl, heterocycloalkyl, aryl or hetaryl, where the alkyl radicals may bear 1, 2, 3 or 4 substituents selected from among cycloalkyl, heterocycloalkyl, aryl, hetaryl, alkoxy, cycloalkoxy, heterocycloalkoxy, aryloxy, alkoxycarbonyl, carboxyl, sulfonyl, NE$^9$E$^{10}$, alkylene-NE$^9$E$^{10}$, NE$^9$E$^{10}$E$^{11+}$X$^-$, halogen, trifluoromethyl, nitro, acyl and cyano and the cycloalkyl, heterocycloalkyl, aryl and hetaryl radicals may bear 1, 2, 3 or 4 substituents selected from among alkyl and the substituents mentioned above for the alkyl radicals R$^{21}$, R$^{22}$ and/or R$^{23}$.

7. A process as claimed in claim 1, wherein the steps (i) to (iv) are carried out in the presence of at least one monodentate phosphine ligands.

8. A method of stabilizing a hydroformylation catalyst system, said method comprising adding at least one monodentate phoshine ligand to the catalyst system essentially in the absence of carbon monoxide and hydrogen, wherein the employed catalyst system comprises at least one metal of transition group VIII and at least one bidentate phosphine.

* * * * *